United States Patent [19]

Andersen et al.

[11] Patent Number: 5,227,132

[45] Date of Patent: * Jul. 13, 1993

[54] STERILIZATION METHOD

[75] Inventors: Harold W. Andersen; William K. Andersen, both of Oyster Bay, N.Y.; Charles H. Harrison, Haw River, N.C.

[73] Assignee: H. W. Andersen Products, Inc., Oyster Bay, N.Y.

[*] Notice: The portion of the term of this patent subsequent to Jun. 26, 2007 has been disclaimed.

[21] Appl. No.: 806,910

[22] Filed: Dec. 12, 1991

Related U.S. Application Data

[60] Division of Ser. No. 483,529, Feb. 22, 1990, Pat. No. 5,118,471, which is a continuation-in-part of Ser. No. 148,408, Jan. 26, 1988, Pat. No. 4,937,046.

[51] Int. Cl.$^5$ .............................................. A61L 2/20
[52] U.S. Cl. .......................................... 422/2; 422/1; 422/33; 422/34; 422/294
[58] Field of Search .................... 422/34, 1, 33, 294, 422/2, 28

[56] References Cited

U.S. PATENT DOCUMENTS

| | | | |
|---|---|---|---|
| 4,937,046 | 6/1990 | Andersen et al. | 422/34 |
| 5,082,636 | 1/1992 | Andersen | 422/34 X |
| 5,118,471 | 6/1992 | Andersen et al. | 422/34 |
| 5,135,715 | 8/1992 | Andersen | 422/34 X |

Primary Examiner—Robert J. Warden
Assistant Examiner—Amalia Santiago
Attorney, Agent, or Firm—Jordan and Hamburg

[57] ABSTRACT

Apparatus and method for sterilizing articles includes a sealed first enclosure made at least partially of a gas-permeable plastic film and a sealed container releasably containing a gaseous sterilant under pressure, the container being enclosed within the first enclosure. An openable second enclosure made at least partially of a gas-permeable plastic film is also provided and the first enclosure and the articles to be sterilized are disposed in the second enclosure. The sterilant which is characterized by toxicity and flammability when released from its container diffuses from the first enclosure into the second enclosure at a rate capable of establishing sterilization conditions in the second enclosure during a sterilization cycle to thereby effect sterilization of the articles in the second enclosure. A third enclosure is also provided in which the second enclosure containing the articles to be sterilized is disposed. A flushing system introduces a flushing medium into the second enclosure to flush out the sterilizing gas therein during a flushing cycle following completion of the sterilization cycle and conducts the sterilant gas and air to a remote area, whereby the flushing system minimizes the extent of residue sterilant gas in the work surrounding the apparatus.

11 Claims, 6 Drawing Sheets

STERILIZATION METHOD

This is a division of application Ser. No. 07/483,529, filed Feb. 22, 1990, now U.S. Pat. No. 5,118,471 issued Jun. 2, 1992, which is a continuation-in-part of application Ser. No. 07/148,408 filed Jan. 26, 1988, now U.S. Pat. No. 4,937,046 issued Jun. 26, 1990.

The invention relates to a sterilization system and particularly to a sterilization system having a post sterilizing flush cycle.

BACKGROUND OF THE INVENTION

A prior art sterilization system is described in U.S. Pat. No. 3,476,506, issued Nov. 4, 1969. This prior art patent discloses an ampule or source of sterilant, a gas release bag which contains the ampule, a liner bag which contains the gas release bag and the items to be sterilized, and a metal container which contains the liner bag. Ethylene oxide sterilizing gas from the ampule is released into the gas release bag and the sterilization gas in the gas release bag is released into the liner bag to sterilize items within the liner bag. After a period of time (e.g. 4 hours), virtually all of the gas that is contained within the ampule is diffused from the inside of the gas release bag into the liner bag, where it is held in contact with the items to be sterilized for the duration of the sterilizing cycle (e.g. 12 hours). During this time,, a significant portion of the gas is gradually released by the liner bag gas diffusion membrane into the space between the liner bag and the metal container. This gas escapes from the unsealed metal container into the ambient work area.

One problem with this prior art sterilization system was that the operator is exposed to the sterilizing gas in the work area and to the gas in the liner bag when the latter is opened upon completion of the sterilization cycle. This problem is overcome in the present invention by utilizing a post sterilization flush which minimizes the extent of residue sterilant in the surrounding work area.

SUMMARY OF THE INVENTION

According to the present invention, an apparatus for sterilizing articles includes a sealed first enclosure made at least partially of a gas permeable plastic film and a sealed container releasably containing a gaseous sterilant under pressure, the container being enclosed within the first enclosure. An openable second enclosure made at least partially of a gas permeable plastic film is also provided and the first enclosure and the articles to be sterilized are disposed in the second enclosure. The sterilant which is characterized by toxicity and flammability when released from its container diffuses from the first enclosure into the second enclosure at a rate capable of establishing sterilization conditions in the second enclosure during a sterilization cycle to thereby effect sterilization of the articles in the second enclosure. A third enclosure is also provided in which the second enclosure containing the articles to be sterilized is disposed. A flushing system introduces air into the second enclosure to flush out the sterilizing gas therein into the third enclosure during a flushing cycle following completion of the sterilization cycle, and an exhaust system exhausts the sterilant gas and air from the third enclosure during the flushing cycle and conducts the exhausted sterilant gas and air to a remote area, whereby the flushing system and the exhaust system minimize the extent of residue sterilant gas in the work area surrounding the apparatus.

In an alternative embodiment of the invention, a flushing cycle is achieved by a flushing system including flushing means for introducing a flushing medium into the second enclosure following completion of the sterilization cycle and for exhausting sterilant gas and the introduced flushing medium from the second enclosure directly to a remote area outside of the enclosed area. The flushing means also includes exhaust means for continuously exhausting air and sterilant gas from the third enclosure to the remote area during the sterilization and flushing cycles. The flushing system minimizes the extent of residue sterilant gas in the enclosed work area surrounding the apparatus.

The method of the present invention includes the steps of containing a volatile sterilant with a sealed first enclosure made at least partially of a gas permeable membrane, disposing the sealed first enclosure and the items to be sterilized within a second enclosure made at least partially of a gas permeable plastic film, disposing the second enclosure within a third enclosure, effecting a sterilizing cycle by releasing the sterilant from the first container in gaseous form, passing the gaseous sterilant into the second enclosure by diffusion through the gas permeable membrane, maintaining sterilizing conditions in the second enclosure to effect sterilization of the items to be sterilized in the second enclosure, passing the gaseous sterilant from the second enclosure to the third enclosure by diffusion through the gas permeable film, effecting a flushing cycle subsequent to the sterilizing cycle by introducing air into said second enclosure to flush out the sterilizing gas from the second enclosure into the third enclosure, exhausting the sterilizing gas and air from the third enclosure, and conducting the exhausted sterilizing gas and air to a remote area, whereby the flushing cycle minimizes the extent of residue sterilant gas in the ambiance.

In an alternative embodiment of the invention, the method effects a flushing cycle subsequent to the sterilizing cycle by introducing a flushing medium into the second enclosure following completion of the sterilizing cycle and exhausting sterilant gas and the introduced flushing medium from the second enclosure directly to a remote area outside of the enclosed area. Air and sterilant gas are continuously exhausted from the third enclosure to the remote area during the sterilizing and flushing cycle. The amount of residue sterilant gas in the enclosed area is thus minimized.

BRIEF DESCRIPTION OF THE DRAWINGS

The above advantages and subsequent description will be more readily understood by reference to the following drawings.

DESCRIPTION OF THE PREFERRED EMBODIMENTS

Figure 1:
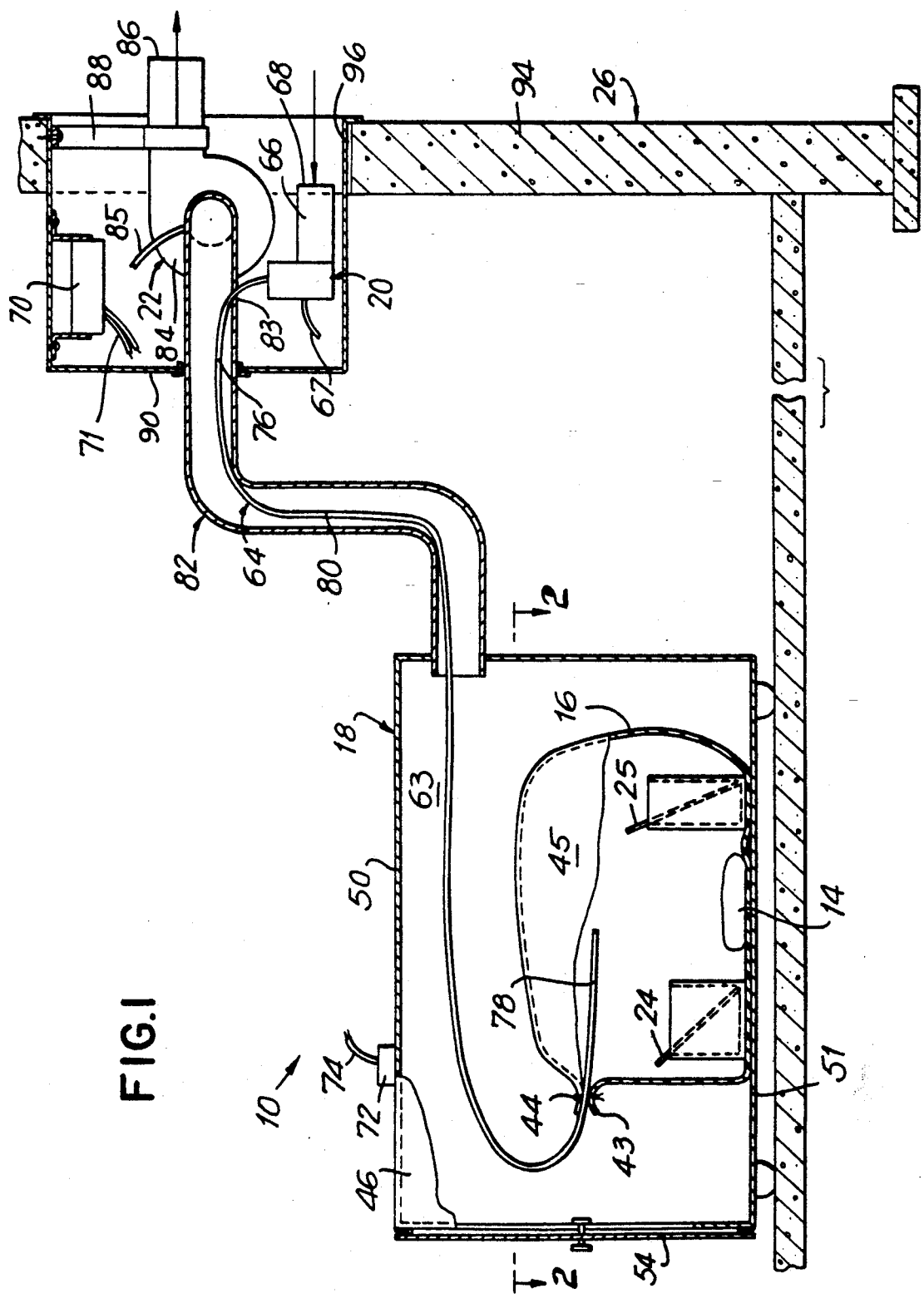
FIG. 1 is a section view as taken through a sterilization system according to the invention.
Figure 2:
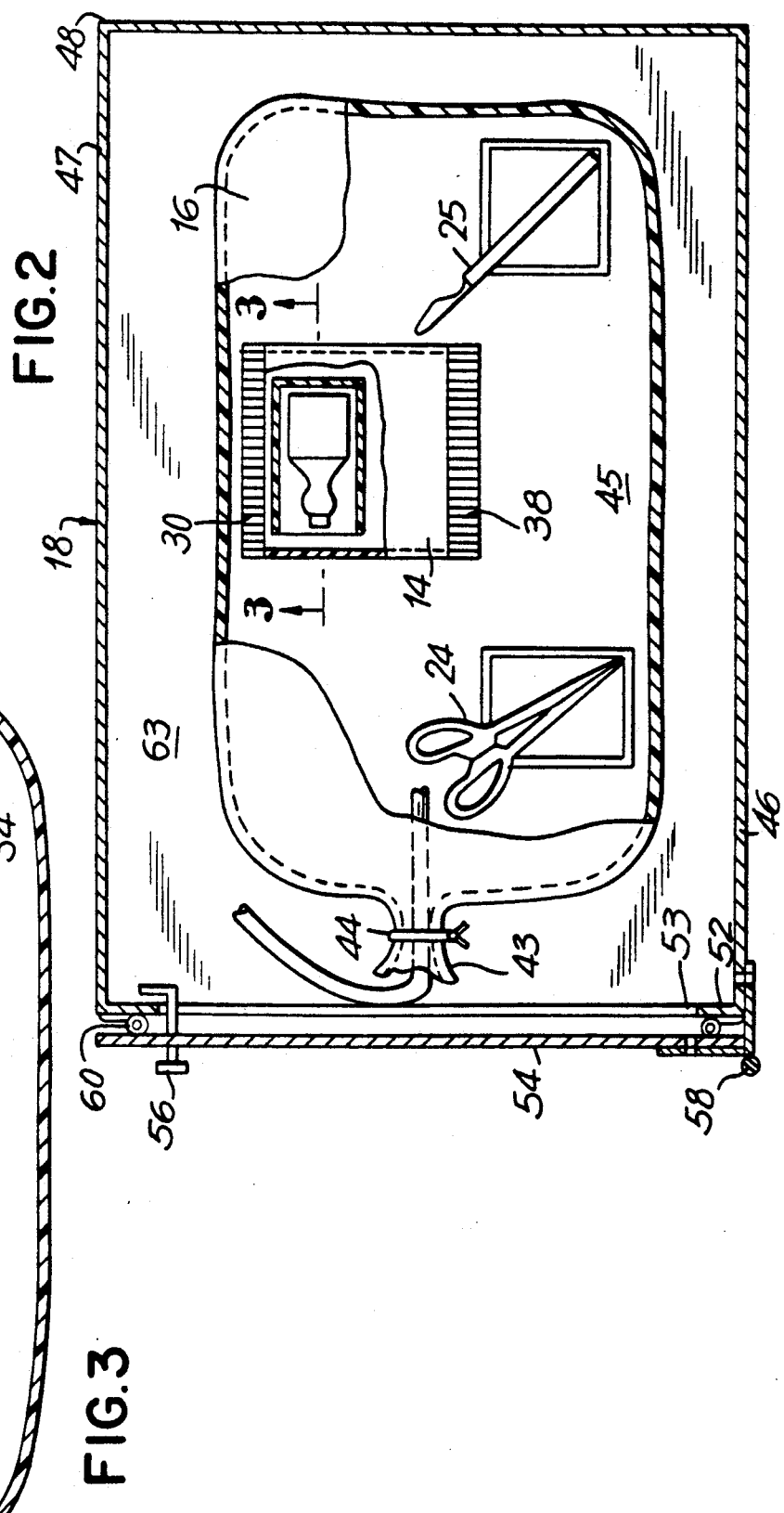
FIG. 2 is a section view as taken along the line 2—2 of FIG. 1.
Figure 3:
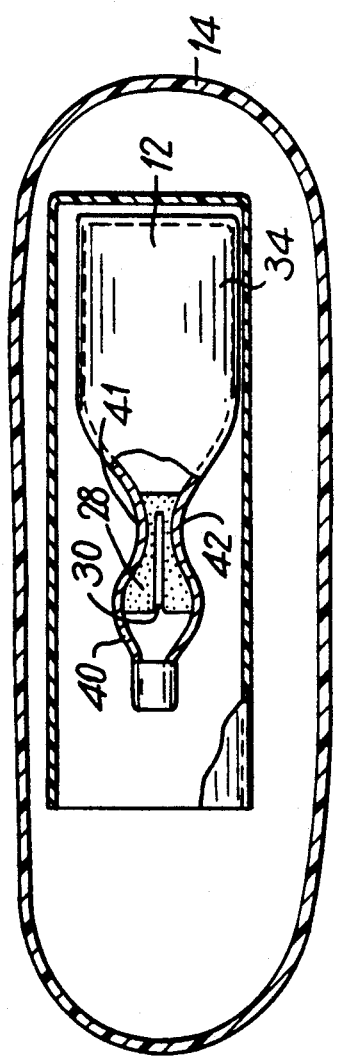
FIG. 3 is a section view as taken along the line 3—3 of FIG. 2.

Referring to FIGS. 1 to 3 in the drawings, there is shown a sterilization system 10 shich includes an ampule or source of sterilant 12, a gas release bag 14 in which the sealed ampule is disposed, a liner bag or second enclosure 16 which contains the gas release bag 14 and the items to be sterilized, and a housing or third enclosure 18. System 10 also includes an air supply means or assembly 20 which connects to the liner bag 16 within the housing 18. System 10 also includes an air and gas exhaust means or assembly 22 which connects to the housing 18. Housing 18 is disposed in an enclosure such as a building 26.

The previously-mentioned U.S. Pat. No. 3,476,506, which is incorporated herein by reference, more fully describes ampule 12, gas release bag 14 and liner bag 16.

Ampule 12 contains ethylene oxide 34 in a liquid state which escapes into gas release bag 14 when ampule 12 is broken. Ampule 12 also has a sealed portion 32 which is sealed after the ethylene oxide 34 is deposited inside the ampule 12. Ampule 12 is placed inside a protective sleeve 36 after it is filled and sealed.

After ampule 12 is placed in sleeve 36, ampule 12 and sleeve 36 are placed in gas release bag 14. The bag 14 is then sealed or closed, for example by sealing one of its end portions 38 or 39.

Ampule 12 has a spout 40 which has a score line 41 that is located at the narrow neck portion 42 of ampule 12. When required, spout 40 is broken manually, in order to release ethylene oxide gas into the gas release bag 14.

Gas release bag 14 is made of a semi-permeable material, such as a polyethylene film, which releases or diffuses the ethylene oxide 34 at a predetermined rate into the liner bag 16 in order to sterilize instruments 24, 25 inside liner bag 16.

Liner bag 16 has a neck portion 43 which has a twisted wire 44 or other closure for closing neck portion 43. Liner bag 16 has an interior cavity 45 in which gas release bag 14 is placed together with instruments 24, 25.

Housing 18 has side walls 46, 47, a rear wall 48, a top wall 50, a bottom wall 51, and a front wall 52, which has an opening 53 with a door 54. Door 54 has a handle and lock 56 and a hinge 58. A loose fit between the door 54 and the walls of the chamber 63 permits air to leak inwardly to chamber 63. The loose fit provides just enough space for some air to leak into the chamber 63 which is at a pressure less than atmospheric, as will be explained, but not such a large space that the reduced pressure in the chamber 63 cannot be maintained by the exhaust means 22. Alternatively, the loose fit may be dispensed with and the housing may be sealed gas-tight, for example by gasket 60. The housing 18 may be made of metal, e.g. stainless steel.

Chamber 63 is normally maintained at a negative pressure, or less than atmospheric pressure, by exhaust means 22.

Air supply means 20 has an air flush tube 64 and an air pump 66 which has an air inlet opening 68. Air supply means 20 has a timer 70 having a circuit connector 71 and a switch 72 which has a circuit connector 74. Switch 72 is mounted on the housing 18. Air pump 66 has a circuit connector 67 which connects to timer connector 71. Switch connector 74 also connects to timer 70.

Air tube 64 has an end portion 76 which connects to the discharge outlet of air pump 66. Air tube 64 has an opposite end portion 78 which is disposed inside liner bag 16. Air tube 64 has an intermediate portion 80, which extends through housing rear wall 48 and through housing chamber 63 and through neck portion 43 of liner bag 16 to the liner bag cavity 45.

Air and gas exhaust means 22 has an exhaust conduit or hose 82 and an exhaust motor 84 which has an air outlet opening 86. Exhaust motor 84 has a circuit connector 85 which connects to timer 70 for control of exhaust motor 84. Exhaust motor 84 is suitably supported such as by straps 88. Exhaust unit 22 also has a support 90 which supports timer 70, air pump 66 and exhaust pump strap 88.

Intermediate portion 80 of air tube 64 may be disposed within exhaust hose 82. End portion 76 of air tube 64 passes through an opening 83 in exhaust hose 82.

Building 26 may have a wall 94 with a wall opening 96. Wall 94 supports framework 90.

In operation, sterilization is initiated by manually fracturing or breaking off the spout of the glass ampule 12 along the score line 41 preformed around the narrow neck 42 of the ampule. The release bag 14 with the released sterilant is disposed in the liner bag 16 along with the material to be sterilized. The sterilizing gas that is released within the gas release bag 14 is diffused from the gas release bag into the liner bag 16 where it is held in contact with the material to be sterilized for the duration of the sterilizing cycle (e.g. 12 hours). During this time, a significant portion of the sterilizing gas is gradually released from the liner bag 16 into chamber 63 of housing 18. Chamber 63 is maintained at a negative pressure due to the operation of the exhaust motor 84 so that none of the slowly-diffusing gas from the liner bag 16 is allowed to escape into the work space. Thus the sterilizing gas in chamber 63 along with air leaking into chamber 63 about the non-gas-tight door 54 is exhausted through exhaust conduit 82 to exhaust opening 86. At the end of the sterilizing cycle, the air pump 20 is activated to provide a post-sterilization flush cycle. Thus the air pump 20 is activated and fresh air flows through the air flush tube 64 to the interior of the liner bag 16 such that fresh air enters the liner bag 16 to dilute the residual sterilizing gas within the liner bag 16, and when the liner bag 16 is fully inflated, forces the mixture of fresh air and residual sterilizing gas to exit the liner bag 16 at the point where the air supply means enters the liner bag 16, that is, where the air flush tube 64 passes through the mouth of the liner bag 16 and is secured by the twisted wire 44. The use of the twisted wire 44 does not provide a gas-tight seal when the liner bag 16 is fully inflated, such that the mixture of fresh air and residual sterilizing gas exits the liner bag around the non-gas-tight twist closure. The diluted gas mixture in the chamber 63 is exhausted by the exhaust means 22 as previously described.

When the liner bag 16 is eventually opened after completion of the sterilizing cycle and the sterilizing flush cycle, the residual sterilizing gas in liner bag 16 is removed by the exhaust means 22 which continues to operate and it is dissipated harmlessly to the outside atmosphere.

In one embodiment of the system 10, there is a reduction of more than one hundred fold in the residual gas retained by liner bag 16 at the time of opening. For example, the concentration of gas within the liner bag 16 at one end of the twelve-hour sterilizing cycle is 130,000 parts per million in the prior art arrangement without the additional air flush technique. The addition of the air flush technique reduces the residual gas to approximately 1000 ppm within liner bag 16 at the end of the two-hour flush time. With system 10, the escape of ethylene oxide gas into the work space atmosphere is sufficiently low so as to be well below 1 ppm and is typically less than 0.1 ppm.

Exhaust means 22 provides that chamber 63 is at less than atmospheric pressure and assures that none of the slowly-diffusing gas in chamber 63 from liner bag 16 is allowed to escape into the work space. When air pump 66 is activated during the flush cycle, fresh air entering liner bag 16 dilutes the residual sterilizing gas within liner bag 16 and, when liner bag 16 is fully inflated, forces the mixture of fresh air and residual sterilizing gas to exit liner bag 16 through liner bag end portion 43 where air tube end portion 78 enters liner bag 16 as previously described. This diluted gas mixture in liner bag 16 is collected by exhaust means 22. Most of the residual gas that might be released when liner bag 16 is opened, after the sterilization and flush cycle is completed, is also removed by exhaust means 22 where it is harmlessly dissipated through exhaust opening 86 to the atmosphere outside wall 94.

System 10 easily meets a recent United States regulation of the allowable work space atmosphere of a maximum of 1 ppm (time weighted average over 8 hours), and easily meets another regulation with a significant incentive of less than 0.5 ppm.

Alternative embodiments of the present invention are shown in FIGS. 4 to 7.

Figure 4:
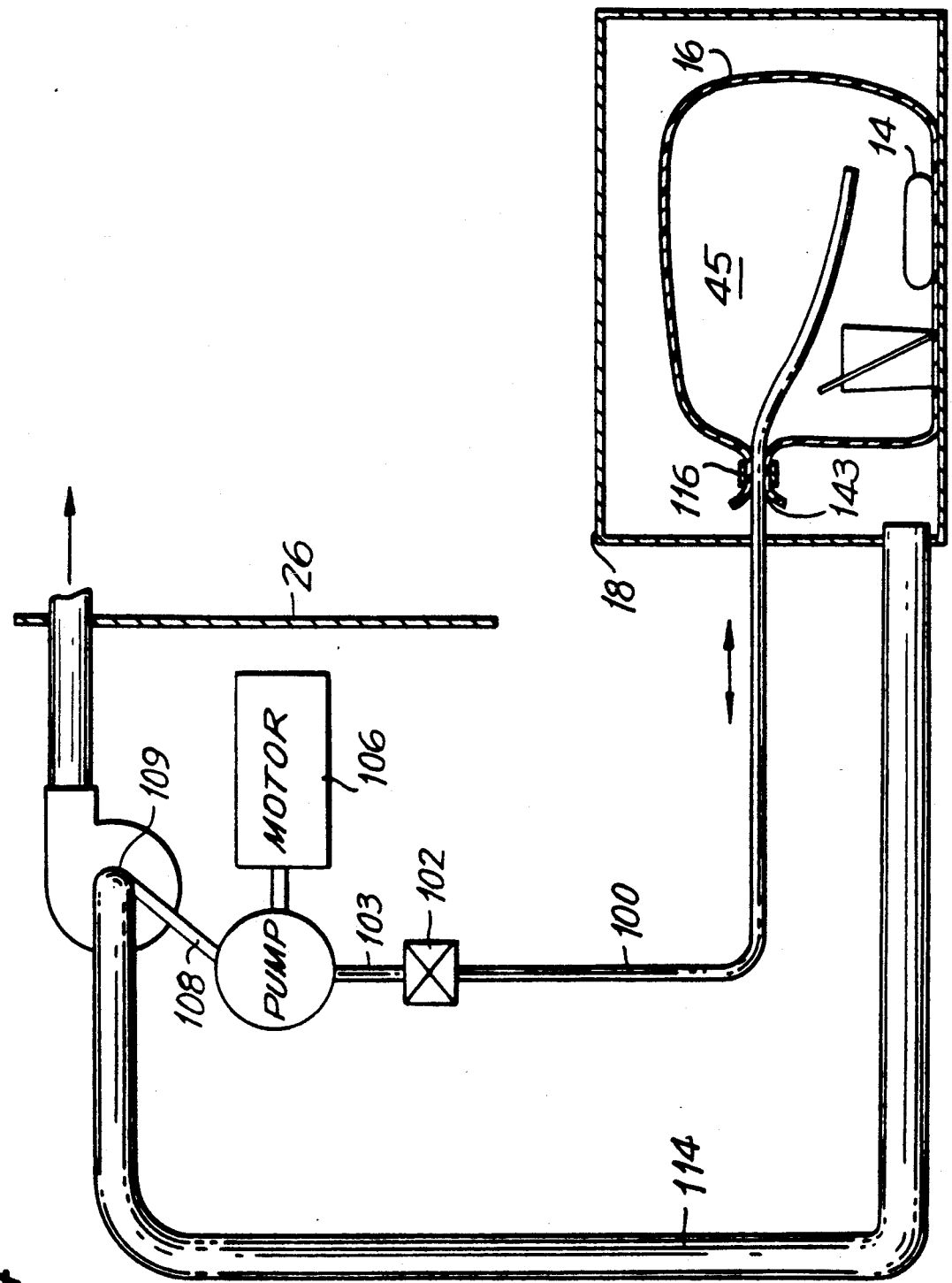
FIG. 4 is a schematic view of another embodiment utilizing a reversible pump.

In the embodiment shown in FIG. 4, a flushing system includes a conduit 100, a valve (e.g., solenoid valve) 102, a conduit 103, a reversible pump 104 driven by a reversible motor 106, a conduit 108, exhaust fan 110 and conduit 112. Air exhaust means includes a conduit 114 interconnecting third enclosure 18 and the exhaust fan 110. The exhaust fan 110 discharges into conduit 112, which leads outside the building 26.

Conduit 100 is arranged in the opening 43 of liner bag 16 to communicate with the interior 45 thereof. Clamp 116 is arranged at the opening 43 of liner bag 16 to provide a gas-tight seal around conduit 100.

When the sterilization cycle is completed, motor 106 is turned on and valve 102 is opened such that pump 104 pumps flushing medium from the inlet 109 of the exhaust fan 110 through the sequentially connected conduit 108, pump 104, conduit 103, valve 102 and conduit 100 into liner bag 16 to flush the liner bag 16. Subsequently, motor 106 is reversed and pump 104 evacuates air and toxic sterilant from liner bag 16 sequentially through conduit 100, valve 102, conduit 103, pump 104, and conduit 108 to the inlet 109 of exhaust fan 110, where it is exhausted through conduit 112 to a remote area outside of the enclosed work area.

The conduit 108 leads to the inlet 109 of the exhaust fan 110. When the pump motor 106 operates in the reverse direction to exhaust the liner bag 16, the pump 104 discharges into the exhaust fan inlet 109 and then passes through the exhaust fan 110 to discharge through the conduit 112. The exhaust fan 106 operates during the flushing cycle so that the contents of liner bag 16 pass through pump 104 and exhaust fan 110 to be discharged outside of the building 26.

When the pump motor operates in the forward direction, the pump 104 draws in flushing medium from the exhaust fan inlet 109 and discharges the flushing medium into the liner bag 16. The flushing medium at the suction 109 of the exhaust fan contains some sterilant inasmuch as the exhaust fan inlet 109 is also in communication with the interior of the third enclosure 18 via the conduit 114. However, as will be explained later, the amount of sterilant at the exhaust fan inlet 109 is so minimal that it would not adversely affect its use as a flushing medium for flushing the interior of the liner bag 16.

Reversible pump 104 alternately pumps flushing medium into and then out of liner bag 16 to effect a flushing action for removing sterilant from liner bag 16. This alternating pump sequence is repeated sequentially until the sterilant gas residue in liner bag 16 has been reduced to an acceptable level. The level of sterilant in the liner bag 16 may have a peak of about 150,000 ppm, for example, one hour after start of the sterilizing cycle. However by way of example, after a sequence of about 30 flushes over a period of about two hours, the level of sterilant gas in liner bag 16 is reduced to less than about 100 ppm. Conversely, without the flushing sequence just described, the level of sterilant gas in liner bag 16 at the end of the sterilization cycle would be in the order of 10,000 to 30,000 ppm. Accordingly, the flushing cycle can reduce the level of sterilant in liner bag 16 from about 10,000 to 30,000 ppm to under 100 ppm.

Exhaust fan 110 operates continuously, during both the sterilization cycle and the flush cycle, to exhaust sterilant gas and air from housing 18 and sequentially through conduit 114, exhaust fan 110 and conduit 112 to a remote area outside of the enclosed work area. The valve 102 is closed during the sterilizing cycle to isolate the interior of the liner bag 16 from the pump 104 during the sterilizing cycle.

The level of sterilant in housing 18 is at a very low level, e.g., about 2 to 10 ppm, because of the controlled release from the liner bag 16 and because of the continuous exhaust through conduit 114, fan 110 and conduit 112. Thus the air withdrawn through conduit 114 by the exhaust fan 110 has a low level of sterilant, and this same air can therefore be passed through the inlet 109 of exhaust fan 110 to the conduit 108 and pump 104 to be utilized as the flushing medium for flushing liner bag 16 during the flushing cycle.

As in the embodiment shown in FIG. 2, the container 18 is provided with an access door which is provided with a loose fit between the door and the walls of the container 18 to permit air to leak into the container 18.

Figure 5:
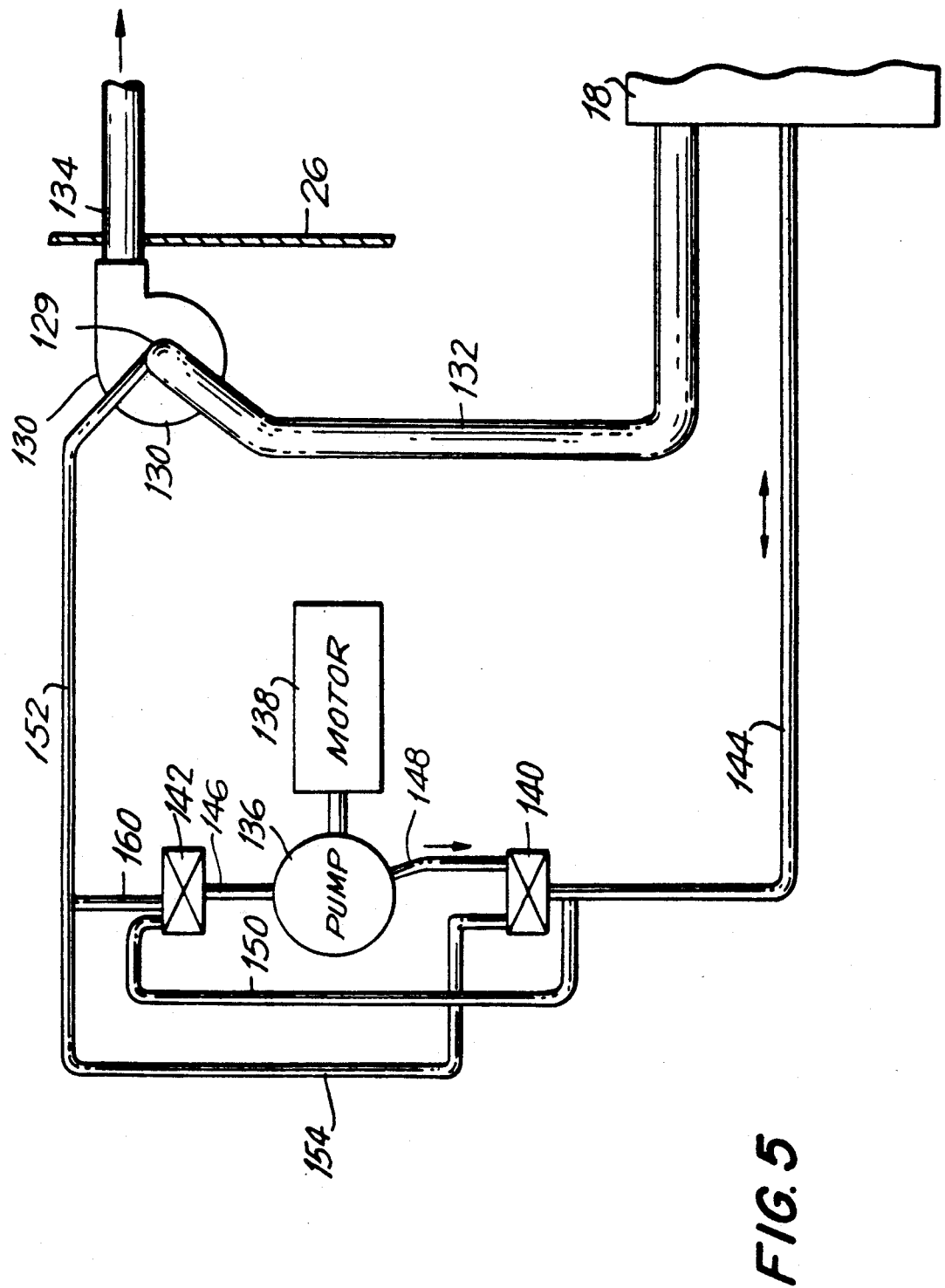
FIG. 5 is a schematic view of a further embodiment of a sterilization system according to the invention utilizing a one-way pump with valve means.

In the embodiment shown in FIG. 5, a flushing system is constructed with a valving mechanism rather than a reversible pump such as the pump 104 in the FIG. 4 embodiment.

As shown in FIG. 5, and similarly to the FIG. 4 embodiment, an exhaust fan 130 operates continuously, during both the sterilization cycle and the flush cycle, to exhaust sterilant gas and air from housing 18 sequentially through conduit 132, exhaust fan 130 and conduit 134 to a remote area outside of the building 26 or outside of the enclosed work area.

The flushing system includes a pump 136 driven by motor 138, a first three-way valve 140, a second three-way valve 142 and an associated interconnecting conduit system. The valves 140 and 142 may be solenoid operated.

In the conduit system, conduit 144 leading from the interior of the liner bag 16 is connected to valve 140 and to the opening 43 of liner bag 16 to communicate with the interior thereof (as shown in FIG. 4). As in the FIG. 4 embodiment, a clamp 116 is provided at the opening 43 of liner bag 16 to form a closure and gas-tight seal around conduit 144.

The conduit system also includes conduit 146 interconnecting the valve 142 with the inlet of pump 136, a conduit 148 interconnecting the outlet of pump 136 with the valve 140, and a conduit 150 interconnecting conduit 144 and valve 142. A discharge/inlet conduit 152 has one end connected to the inlet 129 of exhaust fan 130 and its other end connected to valve 142 through a conduit 160. The conduit system is completed by a conduit 154 interconnecting valve 140 with discharge/inlet conduit 152 and conduit 160.

The flushing system has two modes of operation to alternately provide flushing of liner bag 16 and evacuation of air and sterilant gas from liner bag 16 and transport thereof to a remote area outside of the enclosed work area (for example, outside of the building 26).

In the first mode of operation, valve 140 is set in a position to connect conduit 144 to the outlet of pump 136 through conduit 148 while valve 142 is set in a position to connect the conduits 160, 152 to the inlet of pump 136. In this first mode, liner bag 16 is flushed with flushing medium provided from the inlet 129 of exhaust fan 130, sequentially, through exhaust fan inlet 129, conduits 152, 160, valve 142, conduit 146, pump 136, conduit 148, valve 140 and conduit 144.

After liner bag 16 is flushed with the flushing medium, valves 140 and 142 are each switched to a second position. In the second position, valve 142 is set in a position to connect conduit 14 to the inlet of pump 136 through conduit 150 and conduit 146 while valve 140 is set in a position to connect the outlet of pump 136 to the conduits 148, 154, 152. Air and sterilant gas are evacuated from liner bag 16 sequentially through conduit 144, conduit 150, valve 142, conduit 146, pump 136, conduit 148, valve 140, conduits 154, 152, exhaust fan inlet 129, exhaust fan 130 and conduit 134 to a remote area outside of the enclosed work area.

Valves 140 and 142 may be three-way solenoid-operated valves which may be switched between the first and second positions in a known manner to provide an alternating valve sequence which is repeated sequentially a plurality of times to first flush liner bag 16 with the flushing medium and then evacuate air and sterilant gas from liner bag 16 to a remote are until the sterilant gas residue in liner bag 16 has been reduced to the desired level. The embodiment of FIG. 5 can be operated, for example, to achieve the same reduction in sterilant gas residue in liner bag 16 as described in relation to the FIG. 4 embodiment in that the basic operation is similar except that in FIG. 4, a reversible pump is used and in FIG. 5 a valving system is used to obtain the object of alternately flushing and evacuating the liner bag 16.

Figure 6:
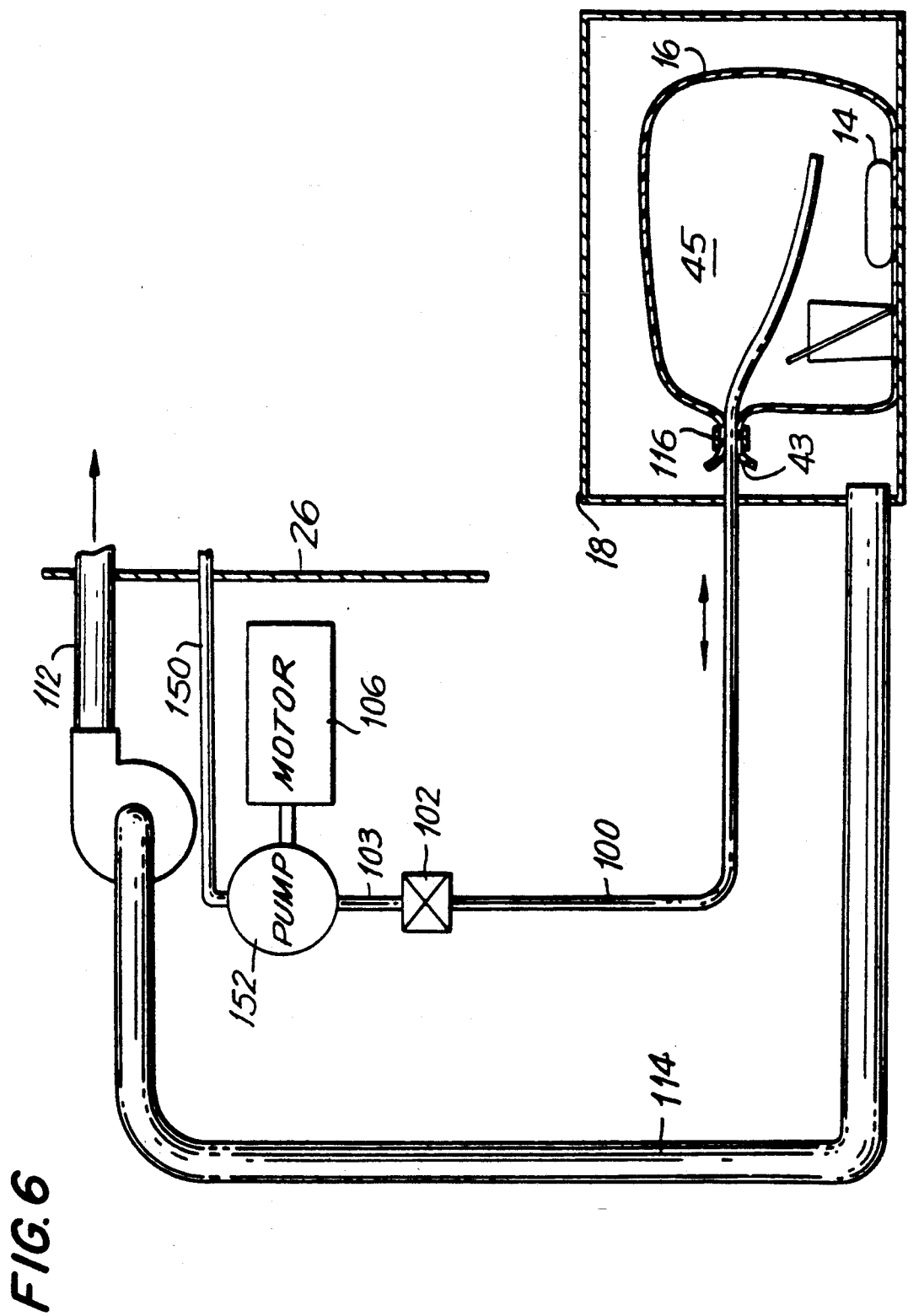
FIG. 6 is a schematic view similar to FIG. 4 of yet another embodiment.

FIG. 6 shows another embodiment which is similar to the FIG. 4 embodiment but wherein a conduit 150 extends from the pump 152 to the remote area outside of the building 26. Thus the conduit 108 in FIG. 4 is replaced by the conduit 150 in FIG. 6. The operation of the FIG. 6 embodiment is similar to the operation of the FIG. 4 embodiment as previously described.

Figure 7:
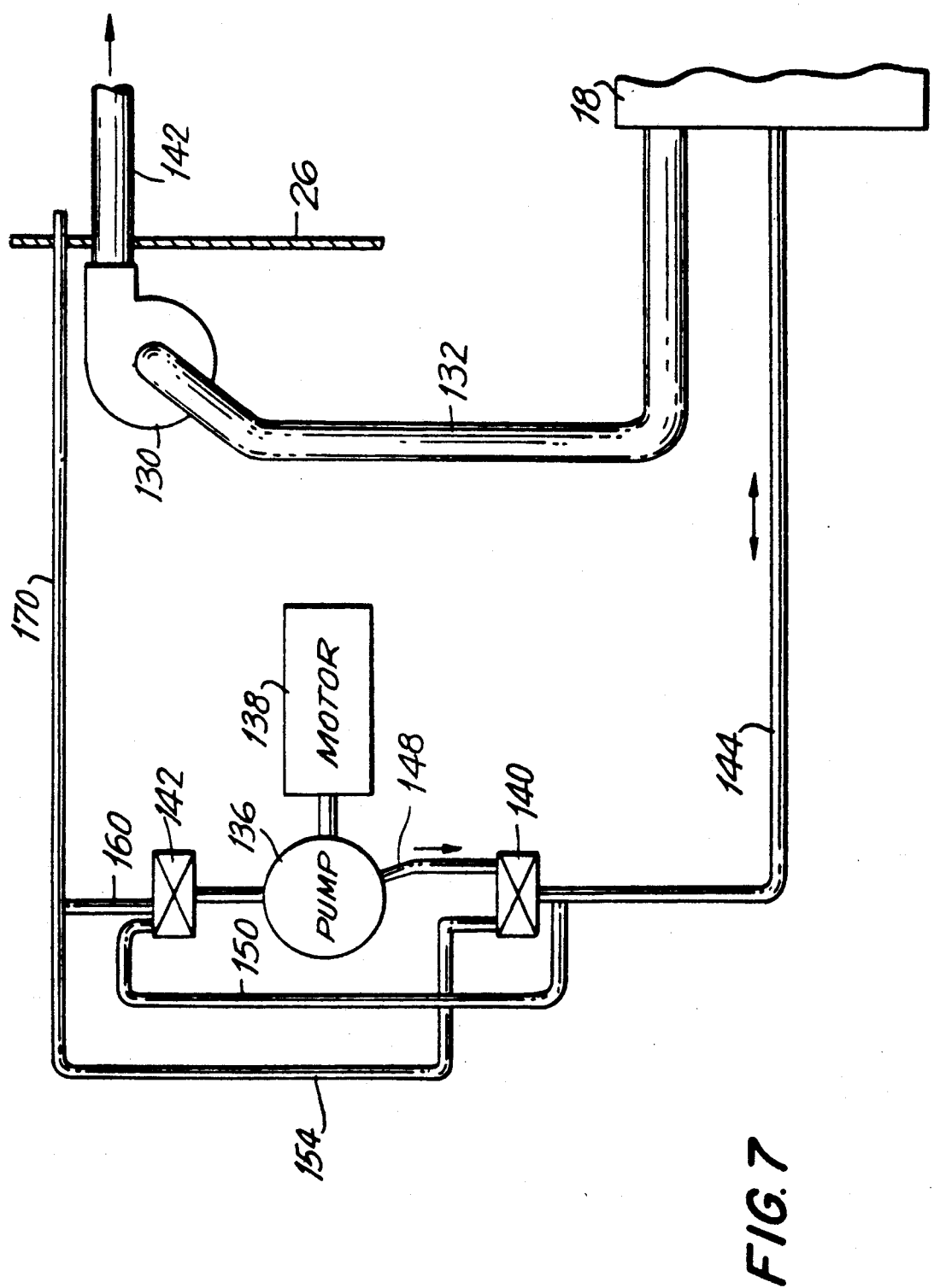
FIG. 7 is a schematic view similar to FIG. 5 of a further embodiment.

FIG. 7 shows a further embodiment which is similar to the FIG. 5 embodiment but wherein a conduit 170 extends from the conduits 154, 160 to the remote area outside the building 26. Thus the conduit 152 in FIG. 5 is replaced by the conduit 170 in FIG. 7. The operation of the FIG. 7 embodiment is similar to the operation of the FIG. 5 embodiment as previously described.

Each of embodiments 4 to 7 is operable to meet the previously-mentioned work space atmosphere of a maximum of 1 ppm (time-weighted average over 8 hours), and easily meets another regulation with a significant incentive of less than 0.5 ppm.

While the invention has been described in its preferred embodiments, it is to be understood that the words which have been used are words of description rather than limitation and that changes may be made within the purview of the appended claims without departing from the true scope and spirit of the invention in its broader aspects.

For example, in the embodiment of FIGS. 1 to 3, a valve means in place of twist wire 44 can be secured to end portion 43 of liner bag 16 so that by manual operation or by automatic operation, the valve means provides a sealed end portion 43 during the sterilizing cycle and provides a venting condition during the following flushing cycle. Venting may be provided by exhaust means 22 during the flush cycle and also upon completion of the flush cycle when the liner bag 16 is opened to thereby vent the residue sterilant gas within the liner bag 16.

The disclosure of parent application U.S. Ser. No. 148, 408 filed Jan. 26, 1988 is hereby incorporated herein by reference.

What we claim is:

1. A method of sterilizing items in an enclosed area comprising the steps of providing a first and second enclosure each made at least partially of a gas-permeable plastic film, providing a third enclosure, containing and sealing a volatile sterilant within said first enclosure, disposing said sealed first enclosure and the items to be sterilized within said second enclosure, disposing said second enclosure within said third enclosure, effecting a sterilizing cycle by releasing the sterilant from said first enclosure in gaseous form, passing said gaseous sterilant into said second enclosure by diffusion through said gas-permeable membrane, maintaining sterilizing conditions in said second enclosure to effect sterilization of said items to be sterilized in said second enclosure, passing the gaseous sterilant from said second enclosure to said third enclosure by diffusion through said gas-permeable film, effecting a flushing cycle subsequent to said sterilizing cycle by alternately and repeatedly introducing a flushing medium into said second enclosure and evacuating sterilant gas and said introduced flushing medium from said second enclosure to a remote area outside of said enclosed area, whereby said flushing cycle minimizes the amount of residue sterilant gas in said enclosed area.

2. A method according to claim 1, further comprising effecting said alternate introduction and evacuation steps by operating a reversible flushing pump in one direction to effect said introduction step and operating said reversible flusing pump means in an opposite direction to effect said evacuation step.

3. A method according to claim 1, comprising effecting said alternate introduction and evacuation steps by changing the operable position of valve means connected with a flushing pump.

4. A method according to claim 1, wherein said alternate introduction and evacuation steps comprise introducing flushing medium from said remote area to said second enclosure and evacuating the contents of said second enclosure to said remote area.

5. A method according to claim 1, further comprising exhausting said third enclosure to said remote area utilizing an exhaust fan during said flushing cycle.

6. A method according to claim 5, wherein said exhaust fan has an inlet, said alternate introduction and evacuation steps comprise introducing flushing medium from the inlet of said exhaust fan to said second enclosure and evacuating the contents of said second enclosure to the inlet of said exhaust fan.

7. A method according to claim 5, further comprising maintaining said third enclosure at a pressure less than atmospheric during said sterilizing and flushing cycles.

8. A method according to claim 5, further comprising admitting ambient air into said third enclosure during said flushing cycle.

9. A method according to claim 5, further comprising effecting said exhausting step continuously during said sterilizing cycle and said flushing cycle.

10. A method according to claim 1, further comprising closing off said second enclosure from said third enclosure during said sterilizing cycle and flushing cycle.

11. A method according to claim 1, further comprising maintaining the level of concentration of residue sterilant in said enclosed area at less than 1 ppm.

* * * * *